US007683024B2

(12) United States Patent
Chan et al.

(10) Patent No.: US 7,683,024 B2
(45) Date of Patent: Mar. 23, 2010

(54) POLYAMINOACIDS FUNCTIONALIZED BY ALPHA TOCOPHEROL AND USES THEREOF, PARTICULAR FOR THERAPEUTIC APPLICATIONS

(75) Inventors: You-Ping Chan, Lyons (FR); Stéphanie Angot, Lyons (FR); Olivier Breyne, Lyons (FR)

(73) Assignee: Flamel Technologies, Venissieuz (FR)

( * ) Notice: Subject to any disclaimer, the term of this patent is extended or adjusted under 35 U.S.C. 154(b) by 46 days.

(21) Appl. No.: 10/516,733

(22) PCT Filed: Jun. 3, 2003

(86) PCT No.: PCT/FR03/50003

§ 371 (c)(1),
(2), (4) Date: Oct. 3, 2005

(87) PCT Pub. No.: WO03/104303

PCT Pub. Date: Dec. 18, 2003

(65) Prior Publication Data

US 2006/0099264 A1 May 11, 2006

(30) Foreign Application Priority Data

Jun. 7, 2002 (FR) .................................. 02 07008

(51) Int. Cl.
*C07K 38/02* (2006.01)
(52) U.S. Cl. .......................... 514/2; 530/324; 530/345; 549/398; 549/410
(58) Field of Classification Search .................... 514/2; 530/324, 345; 549/398, 410
See application file for complete search history.

(56) References Cited

U.S. PATENT DOCUMENTS

| | | | |
|---|---|---|---|
| 2,680,749 A | 6/1954 | Cawley et al. |
| 3,536,672 A | 10/1970 | Fujimoto et al. |
| 4,351,337 A | 9/1982 | Sidman |
| 4,450,150 A | 5/1984 | Sidman |
| 4,600,526 A | 7/1986 | Gallot et al. |
| 4,652,441 A | 3/1987 | Okada et al. |
| 4,766,106 A | 8/1988 | Katre et al. |
| 4,888,398 A | 12/1989 | Bichon et al. |
| 4,892,733 A | 1/1990 | Bichon et al. |
| 4,976,968 A | 12/1990 | Steiner |
| 5,102,872 A | 4/1992 | Singh et al. |
| 5,286,495 A | 2/1994 | Batich et al. |
| 5,399,331 A | 3/1995 | Loughrey et al. |
| 5,449,513 A | 9/1995 | Yokoyama et al. |
| 5,510,103 A | 4/1996 | Yokoyama et al. |
| 5,534,241 A | 7/1996 | Torchilin et al. |
| 5,609,872 A | 3/1997 | Ahlborg et al. |
| 5,780,579 A | 7/1998 | Soula et al. |
| 5,852,109 A | 12/1998 | Makino et al. |
| 5,869,703 A | 2/1999 | Kim et al. |
| 5,872,210 A | 2/1999 | Medabalimi |
| 5,876,969 A | 3/1999 | Fleer et al. |
| 5,904,936 A | 5/1999 | Huille et al. |
| 6,143,314 A | 11/2000 | Chandrashekar et al. |
| 6,153,193 A | 11/2000 | Kabanov et al. |
| 6,180,141 B1 | 1/2001 | Lemercier et al. |
| 6,197,535 B1 | 3/2001 | Bandyopadhyay et al. |
| 6,201,072 B1 | 3/2001 | Rathi et al. |
| 6,235,282 B1 | 5/2001 | Riviere et al. |
| 6,284,267 B1 | 9/2001 | Aneja |
| 6,309,633 B1 | 10/2001 | Ekwuribe et al. |
| 6,313,095 B1 | 11/2001 | Adams et al. |
| 6,320,017 B1 | 11/2001 | Ansell |
| 6,500,448 B1 | 12/2002 | Johnson et al. |
| 6,630,171 B1 | 10/2003 | Huille et al. |
| 7,030,155 B2 * | 4/2006 | Lambert et al. ............. 514/449 |
| 7,226,618 B1 | 6/2007 | Touraud et al. |
| 2001/0000510 A1 | 4/2001 | Sakurai et al. |
| 2003/0133980 A1 | 7/2003 | Costantino et al. |
| 2004/0071716 A1 | 4/2004 | Jansen et al. |
| 2005/0158392 A1 | 7/2005 | Kim et al. |
| 2007/0010652 A1 | 1/2007 | Angot et al. |

(Continued)

FOREIGN PATENT DOCUMENTS

| | | |
|---|---|---|
| EP | 0 179 023 | 1/1991 |
| EP | 0 583 955 | 2/1994 |

(Continued)

OTHER PUBLICATIONS

English Abstract of Huille, WO 00/30618 (Jun. 2000).*
English Abstract of Tourad, Fr 002,801,226 (May 2001).*
Akiyoshi, et al., "Self-Assembled Hydrogel Nanoparticle of Cholesterol-Bearing Pullulan as a Carrier of Protein Drugs: Complexation and Stabilization of Insulin," (1998) *J. Control. Release*, vol. 54, No. 3, pp. 313-320.

(Continued)

*Primary Examiner*—David Lukton
(74) *Attorney, Agent, or Firm*—Patton Boggs LLP

(57) ABSTRACT

The invention concerns novel biodegradable polyaminoacid materials, useful in particular for vectoring active principle(s). The invention also concerns novel pharmaceutical, cosmetic dietetic or phytosanitary compositions based on said polyaminoacids. The invention aims at providing a novel polymer raw material, capable of being used for vectoring active principles and enabling optimal fulfillment of all specified requirements: biocompatibility, biodegradability, easy and inexpensive transformation into particles vectoring active principles, the particles being themselves capable of forming colloidal suspensions, of being easily associated with numerous active principles, and of releasing said active principles in vivo. Therefor, the present invention concerns first of all amphiphilic polyaminoacids comprising aspartic acid units and/or glutamic acid units, characterized in that at least part of said units carry grafts, including at least one alpha-tocopherol motif, for example (polyglutamate or polyaspartate grafted with alpha-tocopherol of synthetic or natural origin).

24 Claims, No Drawings

U.S. PATENT DOCUMENTS

| | | | |
|---|---|---|---|
| 2007/0160568 | A1 | 7/2007 | Angot et al. |
| 2007/0196497 | A1 | 8/2007 | Pouliquen et al. |
| 2007/0248686 | A1 | 10/2007 | Touraud et al. |
| 2007/0265192 | A1 | 11/2007 | Soula et al. |
| 2008/0015332 | A1 | 1/2008 | Bryson et al. |
| 2009/0012028 | A1 | 1/2009 | Chan et al. |

FOREIGN PATENT DOCUMENTS

| | | |
|---|---|---|
| EP | 0 721 776 | 7/1996 |
| EP | 0 734 720 | 10/1996 |
| EP | 0 963 758 | 12/1999 |
| FR | 2 533 209 | 3/1984 |
| FR | 2 732 218 | 10/1996 |
| FR | 2 746 035 | 9/1997 |
| FR | 2 786 098 | 5/2000 |
| FR | 2 801 226 | 5/2001 |
| FR | 2 843 117 | 2/2004 |
| FR | 2 855 521 | 12/2004 |
| FR | 2 860 516 | 4/2005 |
| FR | 2 881 140 | 7/2006 |
| GB | 0 966 760 | 8/1964 |
| JP | 2002-194078 | 7/2002 |
| JP | 2002-194080 | 7/2002 |
| JP | 2003-327693 | 11/2003 |
| WO | WO 87/02219 | 4/1987 |
| WO | WO 87/03891 | 7/1987 |
| WO | WO 88/01213 | 2/1988 |
| WO | WO 89/08449 | 9/1989 |
| WO | WO 91/06286 | 5/1991 |
| WO | WO 91/06287 | 5/1991 |
| WO | WO 96/29991 | 10/1996 |
| WO | WO 96/40279 | 12/1996 |
| WO | WO 97/02810 | 1/1997 |
| WO | WO 97/34584 | 9/1997 |
| WO | WO 98/11874 | 3/1998 |
| WO | WO 99/18142 | 4/1999 |
| WO | WO 99/61512 | 12/1999 |
| WO | WO 00/18821 | 4/2000 |
| WO | WO 00/30618 | 6/2000 |
| WO | WO 00/71163 | 11/2000 |
| WO | WO 00/78791 | 12/2000 |
| WO | WO 01/37809 | 5/2001 |
| WO | WO 02/28521 | 4/2002 |
| WO | WO 02/98951 | 12/2002 |
| WO | WO 02/98952 | 12/2002 |
| WO | WO 03/002096 | 1/2003 |
| WO | WO 2004/13206 | 2/2004 |
| WO | WO 2004/60968 | 7/2004 |
| WO | WO 2004/108796 | 12/2004 |
| WO | WO 2005/33181 | 4/2005 |
| WO | WO 2005/051416 | 6/2005 |
| WO | WO 2007/034320 | 3/2007 |
| WO | WO 2007/051923 | 5/2007 |
| WO | WO 2007/116143 | 10/2007 |

OTHER PUBLICATIONS

Fuller, et al., "A Procedure for the Facile Synthesis of Amino-Acid N-Carboxyanhydrides," (1976) *Biopolymers*, vol. 15, No. 9, pp. 1869-1871.

Tomida, et al., "Convenient Synthesis of High Molecular Weight Poly(Succinimide) by Acid-Catalysed Polycondensation of—Aspartic Acid," (1997) *Polymer*, vol. 38, Issue 18, pp. 4733-4736.

Burton, et al., "Vitamin E: Application of the Principles of Physical Organic Chemistry to the Exploration of its Structure and Function," (1986) Acc. Chem. Res., vol. 19, pp. 194-201.

Poché, et al., "Synthesis and Some Solution Properties of Poly(.Gamma.-Stearyl.alpha.,L-Glutamate)," (1995) Macromolecules, vol. 28, pp. 6745-6753.

In the U.S. Patent and Trademark Office, Non-Final Office Action in re: U.S. Appl. No. 10/130,783, dated Apr. 29, 2005, 10 pages.

In the U.S. Patent and Trademark Office, Final Office Action in re: U.S. Appl. No. 10/130,783, dated Jan. 27, 2006, 14 pages.

In the U.S. Patent and Trademark Office, Non-Final Office Action in re: U.S. Appl. No. 10/574,475, dated Nov. 7, 2008, 5 pages.

In the U.S. Patent and Trademark Office, Final Office Action in re: U.S. Appl. No. 10/398,133, dated Mar. 24, 2009, 8 pages.

In the U.S. Patent and Trademark Office, Final Office Action in re: U.S. Appl. No. 10/516,733, dated Jun. 17, 2008, 7 pages.

In the U.S. Patent and Trademark Office, Non-Final Office Action in re: U.S. Appl. No. 10/398,133, dated Jun. 13, 2008, 11 pages.

In the U.S. Patent and Trademark Office, Non-Final Office Action in re: U.S. Appl. No. 10/398,133, dated Nov. 4, 2005, 9 pages.

In the U.S. Patent and Trademark Office, Non-Final Office Action in re: U.S. Appl. No. 10/398,133, dated Sep. 28, 2007, 14 pages.

In the U.S. Patent and Trademark Office, Non-Final Office Action in re: U.S. Appl. No. 10/516,733, dated Feb. 5, 2007, 6 pages.

In the U.S. Patent and Trademark Office, Non-Final Office Action in re: U.S. Appl. No. 10/516,733, dated Sep. 12, 2007, 7 pages.

In the U.S. Patent and Trademark Office, Non-Final Office Action in re: U.S. Appl. No. 10/574,475, dated Jan. 31, 2008, 8 pages.

In the U.S. Patent and Trademark Office, Non-Final Office Action in re: U.S. Appl. No. 10/580,035, dated Dec. 3, 2008, 25 pages.

In the U.S. Patent and Trademark Office, Final Office Action in re: U.S. Appl. No. 10/580,035, dated Aug. 7, 2009, 16 pages.

In the U.S. Patent and Trademark Office, Non-Final Office Action in re: U.S. Appl. No. 11/878,947, dated Jul. 20, 2009, 11 pages.

Akiyoshi et al., "Self-Assembled Hydrogel Nanoparticle of Cholesterol-Bearing Pullulan as a Carrier of Protein Drugs: Complexation and Stabilization of Insulin," J. Controlled Release, 1998; 54:3, pp. 313-320.

Akiyoshi et al., "Stabilization of Insulin upon Supramolecular Complexation with Hydrophobized Polysaccharide Nanoparticle," *Chemistry Letters*, 1995, No. 8, pp. 707-708.

Bikram et al., "Biodegradable Poly(ethylene glycol)-co-Poly(L-lysine)-g-Histidine Multiblock Copolymers for Nonviral Gene Delivery," *Macromolecules*, 2004; 37, pp. 1903-1916.

Birnbaum et al., "Microparticle Drug Delivery Systems," *Drug Delivery Systems in Cancer Therapy*, 2003; Ch. 6, pp. 117-136.

Burton et al., "Vitamin E: Application of the Principles of Physical Organic Chemistry to the Exploration of its Structure and Function," *Acc. Chem. Res.*, 1986; 19, pp. 194-201.

Candau, S., Chapter 3: Light Scattering, *Surfactant Solutions*, vol. 22, Ed. R. Zana, M. Dekker, Inc. NY (1984) p. 147 - 207.

Constancis et al., "Macromolecular Colloids of Diblock Poly(amino acids) that Bind Insulin," *Journal of Colloid and Interface Science*, 1999, vol. 217, pp. 357-368.

Database WPI Week 200274, AN 2002-685440, Jul. 10, 2002, Derwent Publications Ltd., London, GB.

Database WPI Week 200275, AN 2002-694010, Jul. 10, 2002, Derwent Publications Ltd., London, GB.

Database WPI Week 200425, AN 2002-260230, May 11, 2005, Derwent Publications Ltd., London, GB.

Davies, J.T., "A Quantitative Kinetic Theory of Emulsion Type, I. Physical Chemistry of the Emulsifying Agent," *Proceedings of the Second Interntional Congress of Surface Activity*, 1957; pp. 426-39.

Forssen et al., "Improved Therapeutic Benefits of Doxorubicin by Entrapment in Anionic Liposomes," *Cancer Res.*, 1983; 43:546-550.

Fuller, W.D., A procedure for the facile synthesis of amino-acid n-carboxyanhydrides, *Biopolymers*, 15:1869-71 (1976).

Furumoto et al., "Hepatic Uptake of Negatively Charged Particles in Rats: Possible Involvement of Serum Proteins in Recognition by Scavenger Receptor," *Journal of Controlled Release*, 2004; 97, pp. 133-141.

Gao et al., "Measurement of the Binding of Proteins to Polyelectrolytes by Frontal Analysis Continuous Capillary Electrophoresis," *Anal. Chem.*, 1997; 69:2945-51.

Gatlin et al., "Formulation and Administration Techniques to Minimize Injection Pain and Tissue Damage Associated with Parenteral Products," *Injectable Drug Development, Techniques to Reduce Pain and Irritation*, P.K. Gupta eds., Interpharm Press, Denver, 1999, pp. 401-421.

Gonsalves et al., "Synthesis and Surface Characterization of Functionalized Polylactide Copolymer Microparticles," *Biomaterials*, 1998; 19, pp. 1501-1505.

Handbook of Chemistry and Physics, 88th Ed., 2008 (Viscosities of Liquids) Section 6, pp. 175 - 179).

Harada et al., "Formation of Polyion Complex Micelles in an Aqueous Milieu from a Pair of Oppositely-Charged Block Copolymers with Poly(ethylene glycol) Segments," *Macromolecules*, 1995; 28:5294-99.

Humphrey, M.J., "The Oral Bioavailability of Peptides and Related Drugs," *Delivery System for Peptide Drugs*, Eds. S. Davis et al., Plenum Press, New York, 1986; pp. 139-151.

Illum et al., "Effect of the Nonionic Surfactant Poloxamer 338 on the Fate and Deposition of Polystyrene Microspheres Following Intravenous Administration," *J. Pharm. Sci.*, 1983; 72:9, pp. 1086-1089.

Jaworek et al., "Effects of Analogs of (pyro)Glu-His-Gly-Oh on Food Consumption and Gastric Acid Secretion in Rats," *Life Science*, 1984; 34:26, pp. 2597-2603.

Kataoka, K. "Preparation of Novel Drug Carrier based on the Self-Association of Block Copolymer," *Drug Delivery System*, 1995, vol. 10, No. 5, pp. 363-370.

Kuroda et al., "Hierarchical Self-Assembly of Hydrophobically Modified Pullulan in Water: Gelation by Networks of Nanoparticles," *Langmuir*, 2002; 18, pp. 3780-3786.

Laustsen et al., "The Complete Amino Acid Sequence of Human Placental Oxytocinase," *Biochimica et Biophysica Acta*, 1997, 1352:1, pp. 1-7.

Maa et al., "Spray-Drying of Air-Liquid Interface Sensitive Recombinant Human Growth Hormone," *Journal of Pharmaceutical Sciences*, 1988; 87:2, pp. 152-59.

Oppenheim et al., "The Primary Structure and Functional Characterization of the Neutral Histidine-Rich Polypeptide from Human Parotid Secretion," *Journal of Biological Chemistry*, 1986; 261:3, pp. 1177-1182.

Poché et al., "Synthesis and Some Solution Properties of Poly(y-Stearyl α, L-Glutamate)," *Macromolecules*, 1995; 28, pp. 6745-6753.

Regalado et al., "Viscoelastic Behavior of Semidilute Solutions of Multisticker Polymer Chains," *Macromolecules*, 1999; 32:8580-8588.

Sen et al., "Role of Histidine Interruption in Mitigating the Pathological Effects of Long Polyglutamine Stretches in SCA1: A Molecular Approach," *Protein Science*, 2003; 12, pp. 953-962.

Seo et al., "Phase Transition Behavior and Particle Size Change of pH-Sensitive Imidazole and C18-Grated Poly(asparagine)s," *Controlled Release Society*, 32nd Annual Meeting, June.

Shen, W.C., "Acid Sensitive Dissociative Between Poly (Lysine) and Histamine Modified Poly (Glutamate) as a Model for Drug Releasing From Carriers in Endosomes," 1990, *Biochim. Biophys. Acts.*, 1034(1): 122-24.

Shimura et al., "Fluorescence-Labeled Peptide pI Markers for Capillary Isoelectric Focusing," *Analytical Chemistry*, 2002; 74:5, pp. 1046-1053.

Sohn et al., "Self-Assembly of Substituted Polyglutamates on Solid Substrates: The Side-Chain Effect," *Langmuir*, 1999; 15:5, pp. 1698-1702.

Tomida et al., "Convenient Synthesis of High Molecular Weight Poly(succinimide) by Acid-Catalysed Polycondensation of L-aspartic Acid", *Polymer*, 38: 4733-36 (1997).

Tsutsumiuchi et al., "Synthesis of Polyoxazoline-(Glyco)peptide Block Copolymer Ring-opening Polymerization of (Sugar-Substituted) α Amino Acid N-Carboxyanhydrides with Polyoxazoline Macroinitiators," *Macromolecules*, 1997; 30:4013-17.

Van Heeswijk et al., "The Synthesis and Characterization of Polypeptide-Adriamycin Conjugates and its Complexes with Adriamycin," *J. Controlled Release*, 1985; 1:4, pp. 301-315.

Woodle et al., "Sterically Stabilized Liposomes," *Biochim. Biophys. Acta,* 1992; 1113:2, pp. 171-199.

Woodle, M.C., "Controlling Liposome Blood Clearance by Surface-Grafted Polymers," *Adv. Drug Deliv. Rev.*, 1998; 32:1-2, pp. 139-152.

Yang et al., "Histidine Conjugated Poly(amino acid) Derivatives as the Novel Intracellular Delivery Carrier of an Anticancer Drug," *Controlled Release Society*, 32nd Annual Meeting, Jun. 2005, #254, 2 pages.

Yang et al., "Self-Aggregates of Oligoarginine-Conjugated Poly (Amino Acid) Derivatives as a Carrier for Intracellular Drug Delivery ," 2005, *Biotechol. Let.*, 27 14 :977-82.

Yokoyama et al., "Incorporation of Water-Insoluble Anticancer Drug into Polymeric Micelles and Control of Their Particle Size," *J. Controlled Release*, 1998; 55:219.

French Search Report for No. FR 03-50641, filed Mar. 29, 2004.

International Search Resort for PCT/FR2004/050465 filed Apr. 18, 2005.

International Search Resort for PCT/FR2005/050610, filed Jul. 2, 2006.

* cited by examiner

POLYAMINOACIDS FUNCTIONALIZED BY ALPHA TOCOPHEROL AND USES THEREOF, PARTICULAR FOR THERAPEUTIC APPLICATIONS

This application is a 371 of PCT/FR03/50003, filed Jun. 3, 2003, which claims priority to FR 0207008, filed Jun. 7, 2002.

The present invention relates to novel materials based on biodegradable polyamino acids, which are useful especially for the vectorization of active principal(s) (AP).

The invention is also directed toward novel pharmaceutical, cosmetic, dietetic or plant-protection compositions based on these polyamino acids. These compositions may be of the type allowing the vectorization of AP and preferably being in the form of emulsions, micelles, particles, gels, implants or films.

The APs under consideration are advantageously biologically active compounds that may be administered to an animal or human body via the oral, parenteral, nasal, vaginal, ocular, subcutaneous, intravenous, intramuscular, intradermal, intraperitoneal, intracerebral, buccal, etc. route.

The APs more particularly concerned by the invention, but not limiting the invention thereto, are proteins, glycoproteins, peptides, polysaccharides, lipopolysaccharides, oligonucleotides, polynucleotides and organic molecules. However, they may also be cosmetic products or plant-protection products, such as herbicides, insecticides, fungicides, etc.

In the field of vectorization of active principles, especially medicinal active principles, there is a need, in many cases:
- to protect them against degradation (hydrolysis, precipitation on site, enzymatic digestion, etc.) until they reach their site of action,
- and/or to control their rate of release so as to maintain a constant level over a given period,
- and/or to convey them (while protecting them) to the site of action.

To these ends, several types of polymers have been studied and some are even commercially available. Mention may be made, for example, of polymers of the polylactic, polylacticglycolic, polyoxyethyleneoxypropylene, polyamino acid or polysaccharide type. These polymers constitute starting materials for manufacturing, for example, bulk implants, microparticles, nanoparticles, vesicles, micelles or gels. Besides the fact that these polymers must be suitable for manufacturing such systems, they must also be biocompatible, nontoxic, nonimmunogenic and cost-effective, and they should be easy to eliminate from the body and/or biodegradable. As regards this last aspect, it is furthermore essential that the biodegradation in the body should generate nontoxic products.

By way of illustration of the prior art concerning polymers used as starting materials for making AP vectorization systems, various patents, patent applications or scientific articles are mentioned below.

U.S. Pat. No. 4,652,441 describes polylactide microcapsules encapsulating the hormone LH-RH. These microcapsules are produced by preparing a water-in-oil-in-water emulsion comprising an aqueous inner layer containing the hormone, a substance (gelatin) for fixing said hormone, a polylactide oily layer, and also an aqueous outer layer (polyvinyl alcohol). The AP is released over a period of more than 2 weeks after subcutaneous injection.

U.S. Pat. No. 6,153,193 describes compositions based on amphiphilic poly(oxyethylene)-poly(oxypropylene) micelles, for the vectorization of anticancer agents such as adriamycin.

Akiyoshi et al. (J. Controlled Release 1998, 54, 313-320) describe pullulans that have been made hydrophobic by grafting cholesterol, and which form nanoparticles in water. These nanoparticles, which are capable of reversibility complexing with insulin, form stable colloidal suspensions.

U.S. Pat. No. 4,351,337 describes amphiphilic copolyamino acids based on leucine and glutamate, which may be used in the form of implants or microparticles for the controlled release of active principles. Said active principles are released over a very long period that depends on the rate of degradation of the polymer.

U.S. Pat. No. 4,888,398 describes polymers based on polyglutamate or polyaspartate, and optionally polyleucine, with pendent groups of alkyloxycarbonylmethyl type, placed randomly on the polyamino acid chain. These polyamino acids, grafted with side groups, e.g. methoxycarbonylmethyl, may be used in the form of biodegradable implants containing a sustained-release AP.

U.S. Pat. No. 5,904,936 describes nanoparticles obtained from a polyleucine-polyglutamate block polymer, which are capable of forming stable colloidal suspensions capable of spontaneously associating with biologically active proteins without denaturing them. Said proteins may then be released in vivo in a controlled manner, over a long period.

Patent application WO 00/30618 describes nanoparticles obtained from a poly(sodium glutamate) (polymethyl, ethyl, hexadecyl or dodecyl glutamate) block polymer, which are capable of forming stable colloidal suspensions capable of spontaneously associating with biologically active proteins without denaturing them. Said proteins may then be released in vivo in a controlled manner, over a long period.

These amphiphilic copolyamino acids are modified by the presence of a hydrophobic alkyl side chain.

U.S. Pat. No. 5,449,513 describes amphiphilic block copolymers comprising a polyoxyethylene block and a polyamino acid block, for example poly(β-benzyl-L-aspartate). These polyoxyethylene-polybenzylaspartate polymers form micelles that are capable of encapsulating hydrophobic active molecules such as adriamycin or indomethacin.

Patent application WO 99/61512 describes polylysines and polyornithines functionalized with a hydrophobic group (palmitic acid linked to polylysine or ornithine and a hydrophilic group (polyoxyethylene). These polymers, for example polylysine grafted with polyoxyethylene and palmitoyl chains, form, in the presence of cholesterol, vesicles capable of encapsulating doxorubicin or DNA.

It is moreover known practice to employ vitamin E derivatives, and more specifically α-tocopherol, to construct AP vectorization systems.

Natural vitamin E consists of a mixture of compounds known as tocopherols (see Burton and Ingold, Acc. Chem. Res. 1986, 19, 194-201) and, in this mixture, the α-tocopherol derivative is largely in majority amount. Vitamin E and some of its derivatives are nowadays used as a source of vitamin or as antioxidant in foods and cosmetic products. For these common uses, the vitamin E is found in its D-α-tocopherol, form (its natural form) or in its D-L-α-tocopherol form (racemic and synthetic form). These two products are considered as being essentially nontoxic at doses considerably higher than therapeutic doses. The structure of α-tocopherol is as follows:

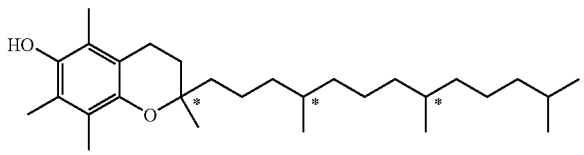

The chiral positions are marked with an asterisk. The natural form has the configurations R,R,R and the synthetic form is a mixture in which the chiral carbons are independently R or S.

As regards the vitamin E derivatives used in the field of vectorization of active principles, there is, at the present time and to the inventors' knowledge, no α-tocopherol-based polymer product, with the exception of polymers of polyoxyethylene type, one end of which is grafted with α-tocopherol-succinate groups. Polyethylene glycol grafted with α-tocopherol succinate at the end of the chain (PEGylated vitamin E) is moreover available on the market, sold under the name TPGS 1000 by the company Eastman Chemical Ltd). This product, patented in 1954 (U.S. Pat. No. 2,680,749), is nowadays used as a source of oral-route vitamin E. This polymer, and similarly α-tocopherol-succinate and unmodified α-tocopherol, have been proposed for the vectorization of active principles.

U.S. Pat. No. 5,869,703 describes similar compounds in which the polyoxyethylene chain comprise α-tocopherol at one end and a (meth)acrylic residue at its other end. These α-tocopherol derivatives are used to prepare stable amphiphilic vesicles (liposomes), used directly in cosmetic applications.

Patent application WO 00/71163 describes formulations based on polyethylene glycol grafted with α-tocopherol-succinate at the end of the chain (TPGS 1000) and on α-tocopherol, for the solubilization of paclitaxel (anticancer product). At the present time, the toxicity associated with the polyoxyethylene part is not known, and it is known that polyoxyethylene is not degraded in vivo. Furthermore, this compound contains only one α-tocopherol unit per polymer chain and it has properties in solution similar to those of surfactants. In any case, the use of this product for vectorization would lead to sparingly stable polymer-active principle combinations.

Patent EP 0 243 446 describes the use of α-tocopherol (hemi) succinate (organic acid derivative of α-tocopherol) for the manufacture of vesicles, in combination with an amine salt. These vesicles may be used for the encapsulation of various active principles including small molecules, peptides and proteins. In general, it is indicated in said patent that the organic acid may be an amino acid or a polyamino acid. However, no details are given in this respect. Only α-tocopherol (hemi) succinates are illustrated.

Thus, even though there are a great many technical solutions in the prior art, developed and proposed for the vectorization of medicinal active principles, meeting all the requirements is difficult to achieve, and remains unsatisfactory.

In this context, one of the essential objectives of the present invention is to provide a novel polymeric starting material, which may be used for AP vectorization and which can optimally satisfy all the specification details:
biocompatibility,
biodegradability,
ability to be converted easily and economically into active principle vectorization particles,
these particles themselves being capable;
of forming stable aqueous colloidal suspensions,
of readily associating with many active principles,
and of releasing these active principles in vivo.

This objective, among others, is achieved by the present invention, which relates firstly to amphiphilic polyamino acids comprising aspartic units and/or glutamic units, characterized in that at least some of these units bear grafts comprising at least one α-tocopherol unit.

These novel polymers have a biodegradable skeleton based on polyamino acids bearing side chains comprising α-tocopherol. These polymers have association and/or encapsulation properties that are surprising in comparison with similar products and, what is more, they are readily degraded in the presence of enzymes.

The Applicant has, to its merit, had the idea of combining, in an entirely judicious and advantageous manner, particular biodegradable polyAsp and/or polyGul polyamino acids with grafts based on α-tocopherol (vitamin E), for the vectorization of AP.

For the purposes of the invention, the term "polyamino acid" covers not only oligoamino acids comprising from 2 to 20 amino acid units, but also polyamino acids comprising more than 20 amino acid units.

Preferably, the polyamino acids according to the present invention are oligomers or homopolymers comprising glutamic or aspartic amino acid repeating units or copolymers comprising a mixture of these two types of amino acid units, said units being partially substituted with grafts comprising α-tocopherol. The units under consideration in these polymers are amino acids having the D, L or D,L configuration and are linked via their α- or γ-positions for the glutamate or glutamic unit and the α- or β-position for the aspartic or aspartate unit.

The preferred amino acid units are those having the L configuration and a bond of $a_l$ type.

Even more preferably, the polyamino acids according to the invention correspond to the general formula (I) below:

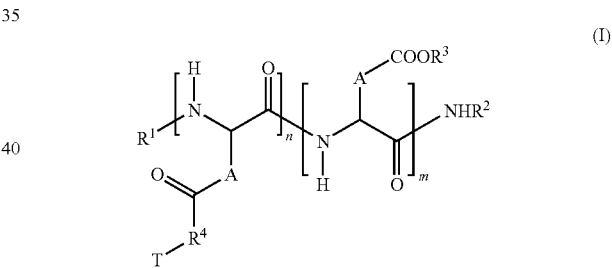

in which:
R$^1$ represents H, a linear C2 to C10 or branched C3 to C10 acyl group, or a pyroglutamate;
R$^2$ represents H, a C2 to C10 linear or C3 to C10 branched alkyl, benzyl or a terminal amino acid unit;
R$^3$ is H or a cationic species preferably selected from the group comprising:
  metallic cations advantageously chosen from the subgroup comprising sodium, potassium, calcium and magnesium,
  organic cations advantageously chosen from the sub group comprising:
    amine-based cations,
    oligoamine-based cations,
    cations based on polyamine (polyethyleneimine being particularly preferred),
    cations based on amino acid(s) advantageously chosen from the class comprising cations based on lysine or arginine,
    or cationic polyamino acids advantageously chosen from the subgroup comprising polylysine or oligolysine;

$R^4$ represents a direct bond or a "spacer" based on 1 to 4 amino acid units;

A independently represented a —$CH_2$— (aspartic unit) or —$CH_2$—$CH_2$— (glutamic unit) radical;

n/(n+m) is defined as the molar degree of grafting and ranges from 0.5 to 100 mol %;

n+m ranges from 3 to 1000 and preferably between 30 and 300;

T represents an α-tocopherol unit.

For these common uses, vitamin E is found in its D-α-tocopherol form (its natural form) or in its D,L-α-tocopherol form (racemic and synthetic form). These two products are considered as being essentially nontoxic at doses considerably higher than therapeutic doses. In the context of the invention, these two forms of α-tocopherol are preferred.

The α-tocopherol is of natural or synthetic origin.

According to a first embodiment of the invention, the polyamino acids are α-L-glutamate or α-glutamic homopolymers.

According to a second embodiment of the invention, the polyamino acids are α-L-aspartate or α-L-aspartic homopolymers.

According to a third embodiment of the invention, the polyamino acids are α-L-aspartate α-L-glutamate or α-L-aspartic/α-L-glutamic copolymers.

Advantageously, the distribution of the aspartic and/or glutamic units bearing grafts comprising at least one α-tocopherol unit is such that the polymers thus composed are either random, or block type or of multi-block type.

According to another mode of definition, the polyamino acids according to the invention have a molar mass of between 2000 and 100 000 g/mol and preferably between 5000 and 40 000 g/mol.

It is moreover preferable for the molar degree of grafting with α-tocopherol of the polyamino acids according to the invention to be between 3% and 70% and preferably between 5% and 50%.

The polyamino acids of the invention are, remarkably, capable of being used in several ways depending on the degree of grafting. The methods for forming a polymer for the encapsulation of an active principle in the various forms targeted by the invention are known to those skilled in the art. For further details, reference may be made, for example, to these few particularly pertinent references:

"*Microspheres, Microcapsules and Liposomes: Vol. 1, Preparation and chemical applications*" Ed. R. Arshady, Citus Books 1999, ISBN: 0-9532187-1-6.

"*Sustained-Release Injectable Products*" Ed. J. Senior and M. Radomsky, Interpharm Press 2000. ISBN: 1-57491-101-5.

"*Colloidal Drug Delivery Systems*" Ed. J. Kreuter, Marcel Dekker, Inc. 1994. ISBN: 0-8247-9214-9.

"*Handbook of Pharmaceutical Controlled Release Technology*" Ed. D. L. Wise, Marcel Dekker, Inc. 2000. ISBN: 0-8247-0369-3.

The polyamino acids are also extremely advantageous as a result of the fact that, at a relatively low degree of grafting of about from 3% to 10%, they form in water at pH 7.4 (for example with a phosphate buffer) colloidal suspensions or gels depending on the polymer concentration. Furthermore, the polyamino acid particles forming the dispersed phase of the colloidal suspension can readily associate with active principles such as proteins, peptides or small molecules. The preferred forming operation is that described in patent application WO 00/30618 by the Applicant, which consists in dispersing the polymer in water and incubating the solution in the presence of an AP. This solution can then be filtered through a 0.02 μm filter and then injected directly into a patient.

Above a degree of grafting of 10%, the polymer can form microparticles capable of associating or of encapsulating APs. In this context, the forming of the microparticles may take place by codissolving the AP and the polymer in a suitable organic solvent, and the mixture is then precipitated from water. The particles are then recovered by filtration and can then be used for an oral administration (in the form of a gel capsule, in compacted and/or coated form, or alternatively in a form dispensed in an oil) or parenterally after redispersing in water.

At degrees of grafting of greater than 30%, the redispersion of the polymer in aqueous phase becomes more difficult due to the smaller amount of ionizable carboxylate functions, and the polymer precipitates. In this case, the polymer can be dissolved in a biocompatible solvent such as N-methylpyrrolidone or a suitable oil such as Miglyol®, and then injected intramuscularly or subcutaneously or into a tumor. The diffusion of the solvent or of the oil results in precipitation of the polymer at the site of injection and thus forms a deposit. These deposits then provide controlled release by diffusion and/or erosion and/or hydrolytic or enzymatic degradation of the polymer.

In general, the polymers of the invention, in neutral or ionized form, may be used alone or in a liquid, solid or gel composition and in an aqueous or organic medium.

It should be understood that the polymer based on polyamino acids contains carboxylic functions that are either neutral (COOH form) or ionized, depending on the pH and composition. For this reason, the solubility in an aqueous phase depends directly on the content of free COOH (not grafted with vitamin E) and on the pH. In aqueous solution, the counter-cation may be a metallic cation such as sodium, calcium or magnesium or an organic cation such as triethanolamine, tris (hydroxymethyl) aminomethane or a polyamine such as polyethyleneimine.

The polymers of the invention are obtained via methods known to those skilled in the art. The polyamino acids may be obtained in at least two ways:

grafting of α-tocopherol onto a polyamino acid, or polymerization of NCA derivatives of α-tocopherol, followed by a selective hydrolysis.

In the first case, a polyamino acid, homopolyglutamate, homopolyaspartate or a glutamate/aspartate copolymer, in block, multiblock or random form, is prepared, for example, according to standard methods.

To obtain polyamino acids of α type, the technique most commonly used is based on the polymerization of N-carboxyamino acid anhydrides (NCA), described, for example, in the article "*Biopolymers, 1976, 15, 1869*" and in the book by H. R. Kricheldorf "*alpha-Aminoacid-N-carboxy Anhydride and related Heterocycles*", Springer Verlag (1987). The NCA derivatives are preferably NCA-O—Me, NCA-O—Et or NCA-O—Bz derivatives (Me=methyl, Et=ethyl and Bz=benzyl). The polymers are then hydrolyzed under suitable conditions to give the polymer in its acid form. These methods are inspired from the description given in patent FR 2 801 226 from the Applicant. A certain number of polymers that may be used according to the invention, for example, of poly(α-L-aspartic), poly (α-L-glutamic), poly (α-D-glutamic) and poly (γ-L-glutamic) type of variable masses are commercially available. The polyaspartic of the α-β type is obtained by condensing aspartic acid (to obtain a poly-succinimide), followed by a basic hydrolysis (see Tomida et al. Polymer 1997, 38, 4733-36).

The coupling of α-tocopherol with an acid function is readily performed by reacting the polyamino acid with vitamin E in the presence of a carbodiimide as coupling agent and, preferably, a catalyst such as 4-dimethyl-aminopyridine, and in a suitable solvent such as dimethylformamide (DMF), N-methylpyrrolidone (NMP) or dimethyl sulfoxide (DMSO). The carbodiimide is, for example, dicyclohexylcarbodiimide or diisopropylcarbodiimide. The degree of grafting is controlled chemically via the stiochiometry of the constituents and reagents, or the reaction time.

In the second case, an NCA derivative of α-tocopherol having the structure below is synthesized. The synthesis is analogous to that described for stearyl glutamate N-carboxyanhydride by Poché et al. *Macromolecules* 1995, 28, 6745-53.

It should be noted that the direct grafting of α-tocopherol onto the polymer takes place via an ester function, whereas in the case of the presence of a spacer based on amino acid(s), it takes place via an amide function. As for the preparation of an ester bond, the amide bond may be formed in the same manner using a standard coupling agent such as a dialkylcarbodiimide.

According to one variant of the invention, the polyamino acids with which it is concerned not only bear α-tocopherol grafts but also, per molecule, at least one graft of polyalkylene glycol type linked to a glutamate and/or aspartate unit, and preferably of formula (II) below:

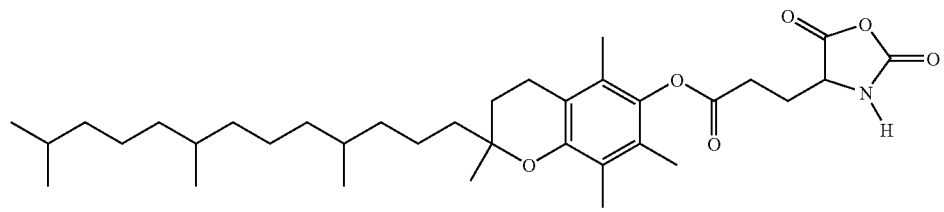

The NCA derivative of α-tocopherol-glutamate is then copolymerized with, for example, benzylglutamate NCA and, to obtain the glutamate or glutamic functions, a selective hydrolysis reaction of the benzyl functions is performed in a mixture of trifluoroacetic acid and hydrobromic acid at room temperature. It should be noted that this second synthetic route makes it possible easily to prepare random, block or multiblock copolymers simply by modifying the order of addition of the monomers.

The coupling of vitamin E via a spacer consisting of 1 to 4 amino acids may be performed via successive reactions of vitamin E with suitably protected amino acids, which are then deprotected to have a graftable amine function on the polymer, or by reaction with an oligopeptide. For example, the synthesis of an α-tocopherol with a leucine unit is performed according to a general method well known to those skilled in the art and according to the following scheme:

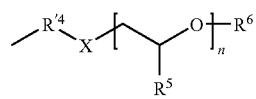

in which
$R'^4$ represents a direct bond or a "spacer" based on 1 to 4 amino acid units;
X is a hetero atom chosen from the group comprising oxygen, nitrogen and sulfur;
$R^5$ and $R^6$ independently represent H or a linear C1 to C4 alkyl.
n ranges from 3 to 1000.

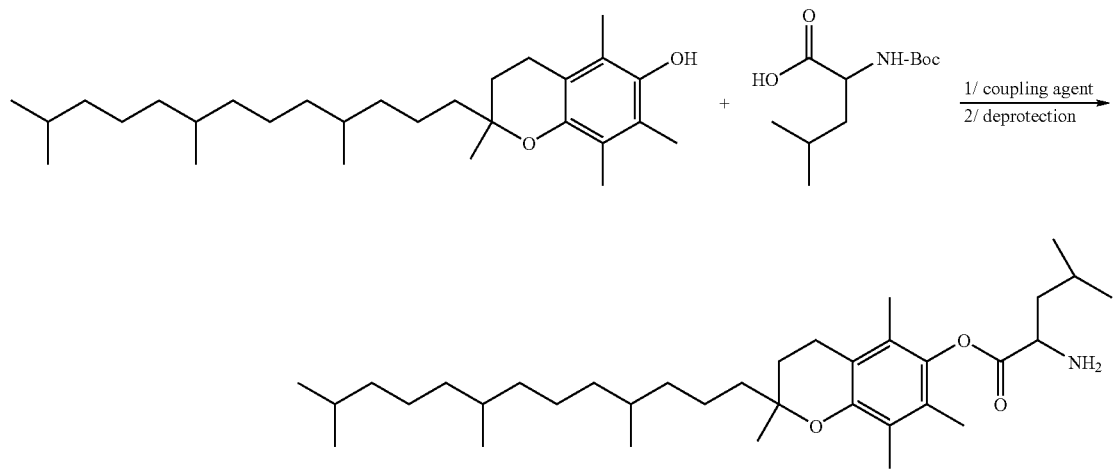

Preferably, the polyalkylene glycol is a polyethylene glycol.

According to another preferred characteristic of the invention, the molar percentage of grafting of the polyalkylene glycol ranges from 1% to 30%.

The grafting of these pendent side groups (II) is performed in a manner that is known per se and according to techniques within the capability of a person skilled in the art, for example by forming amide, ester or thioester bonds with the carboxyls of glutamate and/or aspartate monomers. These techniques may especially be those used for the grafting of α-tocopherol onto a polyamino acid skeleton, said techniques being described in the present patent application.

According to another of its aspects, the invention is directed toward a pharmaceutical, cosmetic, dietetic or plant-protection composition comprising at least one of the polyamino acids as defined above.

According to one advantageous arrangement of the invention, this composition comprises, besides α-tocopherol, at least one active principle, which may be a therapeutic, cosmetic, dietetic or plant-protection active principle.

Preferably, the active principle is a protein, a glycoprotein, a polysaccharide, a liposaccharide, an oligonucleotide, a polynucleotide or a peptide.

Even more preferably, the active principle is a hydrophobic, hydrophilic or amphiphilic organic "small molecule".

According to the present description, the term "small molecule" especially denotes nonprotein molecules.

This composition may be in the form of nanoparticles, microparticles, solutions, emulsions, suspensions, gels, micelles, implants, powders or films.

According to one of its particularly preferred forms, the composition, containing or not containing active principle(s), is a stable colloidal suspension of nanoparticles and/or microparticles and/or micelles of polyamino acids, in an aqueous phase.

The composition according to the invention, when it is pharmaceutical, may be administered via the oral, parenteral, nasal, vaginal, ocular, subcutaneous, intravenous, intramuscular, intradermal, interperitoneal, intracerebral or buccal route.

It may also be envisioned for the composition to be in the form of a solution in a biocompatible solvent, capable of being injected subcutaneously, intramuscularly or into a tumor.

According to another variant, the composition according to the invention is formulated such that it is injectable and such that it is capable of forming a deposit at the site of injection.

The invention is also directed toward compositions comprising polyamino acids according to the invention and active principles, and which are capable of being used for the preparation:

of medicinal products, in particular for oral, nasal, vaginal, ocular, subcutaneous, intravenous, intramuscular, intradermal, intraperitoneal or intracerebral administration, the active principles of these medicinal products possibly being, especially, proteins, glycoproteins, proteins linked to one or more polyalkylene glycol chains {for example polyethylene glycol (PEG), in which case they are referred to as "PEGylated" proteins}, peptides, polysaccharides, liposaccharides, oligonucleotides, polynucleotides and hydrophobic, hydrophilic or amphiphilic organic small molecules;

and/or nutrients;

and/or cosmetic or plant-protection products.

According to yet another of its aspects, the invention is directed toward a process for preparing:

medicinal products, in particular for oral, nasal, vaginal, ocular, subcutaneous, intravenous, intramuscular, intradermal, intraperitoneal or intracerebral administration, the active principles of these medicinal products possibly being, especially, proteins, glycoproteins, proteins linked to one or more polyalkylene glycol chains {for example polyethylene glycol (PEG), in which case they are referred to as "PEGylated" proteins}, peptides, polysaccharides, liposaccharides, oligonucleotides, polynucleotides and hydrophobic, hydrophilic or amiphiphilic organic small molecules;

and/or nutrients;

and/or cosmetic or plant-protection products;

this process being characterized in that it consists essentially in using at least one polyamino acid as defined above and/or the composition itself also described above.

As indicated above, the techniques for associating one or more APs with the α-tocopherol-grafted polyamino acids according to the invention are described especially in patent application WO 00/30618.

The invention also relates to a therapeutic treatment method that consists essentially in administering the composition as described in the present description, via the oral, parenteral, nasal, vaginal, ocular, subcutaneous, intravenous, intramuscular, intradermal, intraperitoneal, intracerebral or buccal route.

According to one particular embodiment, the therapeutic treatment method consists essentially in using a composition as described above in the form of a solution in a biocompatible solvent, and then injecting it subcutaneously, intramuscularly or into a tumor, preferably such that is forms a deposit at the site of injection.

As examples of APs that may be associated with the polyamino acids according to the invention, whether or not they are in the form of (nano or micro) particles, mention may be made of:

proteins such as insulin, interferons, growth hormones, interleukins, erythropoietin or cytokines;

peptides such as leuprolide or cyclosporin;

small molecules such as those belonging to the anthracyclin, taxoid or camptothecin family;

and mixtures thereof.

The invention will be understood more clearly and its advantages and implementation variants will emerge more clearly from the examples that follow, which describe the synthesis of α-tocopherol-grafted polyamino acids, their conversion into an AP vectorization system (stable aqueous suspension of nanoparticles) and demonstration of the capacity of such a system to associate with APs (small organic molecules, proteins, etc.) to form pharmaceutical compositions.

EXAMPLE 1

Polymer P1

Synthesis of a Polyglutamate Grafted with α-tocopherol of Synthetic Origin

The α-L-polyglutamate polymer, with a mass equivalent to about 10 000 relative to a polyoxyethylene standard, is obtained by polymerization of NCAGLuOMe, followed by a hydrolysis, as described in patent application FR 2 801 226. 5.5 g of this α-L-polyglutamate polymer are dissolved in 92 ml of dimethylformamide (DMF), by heating at 40° C. for 2 hours. Once the polymer has dissolved, the temperature is allowed to return to 25° C. and 1.49 g of D,L,α-tocopherol (>98%, obtained from Fluka®) predissolved in 6 ml of DFM, 0.09 g of 4-dimethylaminopyridine predissolved in 6 ml of DMF and 0.57 g of diisopropylcarbodiimide predissolved in 6 ml of DMF are successively added. After stirring for 8 hours at 25° C., the reaction medium is poured into 800 ml of water containing 15% sodium chloride and hydrochloric acid (pH 2). The precipitated polymer is then recovered by filtration, washed with 0.1N hydrochloric acid and then washed with water. The polymer is then redissolved in 75 ml of DMF and then reprecipitated from water containing, as previously, salt and acid at pH2. After washing twice with water, the polymer is washed several times with diisopropyl ether. The polymer is then oven-dried under vacuum at 40° C. A yield of about 85% is obtained.

The degree of grafting estimated by proton NMR is about 7.8% and an HPLC analysis reveals a residual tocopherol content of less than 0.3%.

Mw (measured by GPC, eluting with NMP)=17 500 g/mol (as polymethyl methacrylate equivalent).

EXAMPLES 2, 3, 4 AND 5

Synthesis of Polymers P2, P3, P4 and P5

Polymers containing variable amounts of tocopherol are prepared in the same manner.

TABLE 1

| Polymer | α-Tocopherol | Degree of grafting |
|---|---|---|
| P2 | Synthetic: D, L | 5.2% |
| P3 | Synthetic: D, L | 12.8% |
| P4 | Synthetic D, L | 20.0% |
| P5 | Synthetic D, L | 50.0% |

In all cases, the amount of tocopherol effectively grafted was confirmed by NMR.

EXAMPLE 6

Polymer P6

Synthesis of a Polyglutamate Grafted with α-tocopherol of Natural Origin

In a similar manner, the polymer P6 is synthesized with 7.3% of D-alpha-tocopherol of natural origin (at a purity of 98.5%, obtained from the company ADM France). The molar mass is 17 400 (GPC NMP, PMMA eq).

EXAMPLE 7

Analysis of the Polymers in Aqueous Solution

The polymers are dissolved in a phosphate-buffered saline at pH 7.4 at concentrations ranging from 10 to 40 mg/ml, and the pH is adjusted to 7.4 by adding 0.1N sodium hydroxide. The dissolution is observed visually.

TABLE 2

Solubility in saline water at pH 7.4

| Polymer | Degree of grafting | Concentration | Appearance |
|---|---|---|---|
| P1 (D, L) | 7.8% | 10 to 30 mg/ml | soluble and clear |
| P3 (D, L) | 12% | 10 mg/ml | very fine precipitate |

TABLE 2-continued

Solubility in saline water at pH 7.4

| Polymer | Degree of grafting | Concentration | Appearance |
|---|---|---|---|
| P4 (D, L) | 20% | 10 mg/ml | very fine precipitate |
| P6 (D) | 7.3% | 10 to 30 mg/ml | soluble and clear |

Phosphate buffer: 0.01M phosphate, 0.0027M KCl and 0.137M NaCl.

An observation by electron transmission of the clear solutions of the polymer P1 deposited on a support shows the existence of nanoparticles of 15 to 25 nm. A comparative analysis of the solutions of polymer P1, P6 and α-tocopherol succinate at 15 mg/ml in water at pH 7.4 (phosphate buffer) reveals that only the α-tocopherol succinate develops a milky solution characteristic of vesicles, as described in patent EP 0 243 446.

EXAMPLE 8

Adsorption of a Dye onto the Polymer P1

According to one of the subjects of the invention, the polymers may be used in the form of a colloidal suspension in water and associated with an active principle. For this application, it is demonstrated in the experiment below that with certain polymers, especially those with a degree of grafting of about from 5% to 10% tocopherol, the adsorption capacity is greater than that of a similar compound of the prior art.

For this study, the polymer P1 was compared with a similar polymer containing a dodecanol chain grafted onto a polyglutamate. This polymer is described in patent WO 00/30618.

The study is performed in the following manner: the polymers are dissolved in an aqueous solution at pH 7 (phosphate buffer) and 5 mg of the dye known as Orange OT (Rn CAS: 2646-17-5) are added. The solutions are left in an ultrasonic bath for 1 hour to achieve the association. The solutions are then centrifuged to remove the nonassociated dye, and the optical density is measured at the λmax of the dye, which is at 495 nm.

TABLE 3

| Polymer | Degree of grafting | Polymer concentration | Normalized OD |
|---|---|---|---|
| P1 (α-tocopherol) | 7.8 mol % | 13.8 mg/ml | 1 |
| Comparative polymer* (dodecanol) | 15 mol % | 17.3 mg/ml | 0.45 |

*WO 00/30618

It is found that at a molar degree of grafting of less than a half and at a slightly smaller mass concentration of polymer, the polymer P1 has a much higher capacity for association of the dye Orange OT.

EXAMPLE 9

Synthesis of the Polymer P7

Synthesis of a Polyglutamate Containing an α-tocopherol Leucine Graft

The α-tocopherol leucine derivative is first synthesized, in the following manner. D,L-α-Tocopherol (4.3 g) is reacted with BOC-leucine (2.3 g) in 15 ml of dichloromethane in the presence of 4-dimethylaminopyridine (244 mg) and diisopropylcarbodiimide (1.5 g). After 2 hours at 30° C. the product is purified by filtration on a column of silica. 5 g of the product α-tocopherol leucine BOC are obtained (77% yield). Its structure is confirmed by NMR spectroscopy. The deprotection of the product is performed in trifluoroacetic acid at a temperature of between 5 and 10° C. for 1 hour. After purification by filtration through silica, 3.3 g of the desired product are isolated (78% yield). Its structure is confirmed by NMR spectroscopy.

The grafting reaction on a polyglutamic acid is then performed under the same conditions as in example 1, with a degree of grafting of 7%. The structure of the polymer and the degree of grafting were confirmed by NMR spectroscopy.

EXAMPLE 10

Synthesis of Polymer P8

Synthesis of a polyglutamate containing an α-tocopherol graft and a polyoxyethylene glycol graft.

A grafting reaction is performed as in example 1, with 11 mol % of α-tocopherol and 2 mol % of an amino methoxypolyethylene glycol of formula $MeO(CH_2CH_2O)_a CH_2CH_2NH_2$ and of molar mass 3000 (product obtained from the company Shearwaters). The polymer in its acid form is obtained in a yield of 72%. Proton NMR confirms a degree of grafting with α-tocopherol of 10.9% and with polyethylene glycol of 1.9%.

EXAMPLE 11

Adsorption of Insulin

A solution containing 1 mg of polymer P1 and 7 mg of insulin at pH 7.0 in 1 ml of water is prepared and is left to incubate for 2 hours. The suspension is then ultrafiltered (10 000×G, 20 minutes with a 100 KDa threshold). The free insulin in the filtrate is assayed by HPLC and the amount of associated insulin is deduced by difference. A degree of association of greater than 95% relative to the insulin employed is measured. Under the same conditions, the comparative polymer of example 8 allows 40% association. The adsorption capacity of polymer P1 is thus greater.

EXAMPLE 12

In-vitro Degradation of Polymer P1 in the presence of Enzymes

Polymer P1 is dissolved at pH 7.5 (phosphate buffer and 10 mM of calcium cation) and at a concentration of 20 mg/ml. 0.1 ml of protease (solution of 10 mg/ml) is added and the degradation is monitored by aqueous GPC.

A relatively rapid degradation is found, with a half-life time of the initial polymer of about 100 minutes.

The invention claimed is:

1. A polyamino acid comprising aspartic units and/or glutamic units, characterized in that at least some of these units bear side chains comprising at least one α-tocopherol unit.

2. The polyamino acid as claimed in claim 1, characterized by the general formula (I) below:

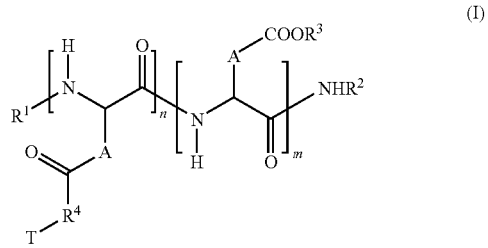

in which:
R¹ represents H, a linear C2 to C10 or branched C3 to C10 acyl group, or a pyroglutamate;
R² represents H, a C2 to C10 linear or C3 to C10 branched alkyl, benzyl or a terminal amino acid unit;
R³ is H or a cationic species selected from the group comprising of:
  metallic cations selected from the subgroup consisting of sodium, potassium, calcium and magnesium,
  organic cations selected from the subgroup consisting of:
    amine-based cations,
    oligoamine-based cations,
    cations based on polyamine,
    cations based on amino acid(s) selected from the class comprising cations based on lysine or arginine,
  and cationic polyamino acids selected from the subgroup consisting of polylysine and oligolysine;
R⁴ represents a direct bond or a "spacer" based on 1 to 4 amino acid units;
A independently represented a —CH₂— (aspartic unit) or —CH₂—CH₂— (glutamic unit) radical;
n/(n+m) ranges from 0.5 to 100 mol %;
n+m ranges from 3 to 1000;
T represents an α-tocopherol unit.

3. The polyamino acid as claimed in claim 1 or 2, characterized in that the α-tocopherol is of natural origin.

4. The polyamino acid as claimed in claim 1 or 2, characterized in that the α-tocopherol is of synthetic origin.

5. The polyamino acid as claimed in claim 2, characterized in that the polyamino acid comprises an α-L-glutamate or α-L-glutamic acid homopolymer.

6. The polyamino acid as claimed in claim 2, characterized in that the polyamino acid comprises an α-L-aspartate or α-L-aspartic acid homopolymer.

7. The polyamino acid as claimed in claim 2, characterized in that the polyamino acid comprises an α-L-aspartate/α-L-glutamate or α-L-aspartic acid /α-L-glutamic acid copolymer.

8. The polyamino acid as claimed in claim 1 or 2, characterized in that the distribution of the aspartic and/or glutamic units that bear side chains comprising at least one α-tocopherol unit is such that the polymers are either random, or of block type, or of multiblock type.

9. The polyamino acid as claimed in claim 1 or 2, wherein the molar mass is between 2000 and 100 000 g/mol.

10. The polyamino acid as claimed in claim 1 or 2, characterized in that the molar degree of grafting is between 3% and 70%.

11. The polyamino acid as claimed in claim 1, wherein the polyamino acid bears at least one graft of polyalkylene glycol.

12. The polyamino acid as claimed in claim 11, wherein the at least one graft of polyalkylene glycol comprises the formula (II) below:

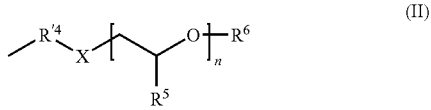

in which:
- $R'^4$ represents a direct bond or a "spacer" based on 1 to 4 amino acid units;
- X is a hetero atom chosen from the group comprising oxygen, nitrogen and sulfur;
- $R^5$ and $R^6$ independently represent H or a linear C1 to C4 alkyl;
- n ranges from 3 to 1000.

13. The polyamino acid is claimed in claim 12, wherein the at least one graft of polyalkylene glycol is a polyethylene glycol.

14. The polyamino acid as claimed in claim 11, characterized in that the molar percentage of grafting of the polyalkylene glycol ranges from 1% to 30%.

15. A composition comprising at least one of the polyamino acids as claimed in any one of claims 1 or 2, and at least one active principle.

16. The composition as claimed in claim 15, characterized in that the active principle is selected from the group consisting of: a protein, a glycoprotein, a polysaccharide, a liposaccharide, an oligonucleotide, a polynucleotide and a peptide.

17. The composition as claimed in claim 15, characterized in that the active principle is a small organic molecule that is hydrophobic, hydrophilic or amphiphilic.

18. The composition as claimed in claim 15, wherein the composition is a pharmaceutical and is administered via the oral, parenteral, nasal, vaginal, ocular, subcutaneous, intravenous, intramuscular, intradermal, intraperitoneal, intracerebral or buccal route.

19. The composition as claimed in claim 15, characterized in that it is in the form selected from the group consisting of a gel, an emulsion, a solution, a suspension, micelles, nanoparticles, microparticles, a powder and a film.

20. The composition is claimed in claim 15, characterized in that it is a colloidal suspension of nanoparticles and/or microparticles and/or micelles of polyamino acids, in an aqueous phase.

21. The composition as claimed in claim 15, characterized in that it is in the form of a solution in a biocompatible solvent and in that it is capable of being injected subcutaneously, intramuscularly or into a tumor.

22. The composition as claimed in claim 15, wherein the composition is a pharmaceutical and is injectable and in that it is capable of forming a deposit at the site of injection.

23. The composition as claimed in claim 15, wherein the composition is used in the preparation of medicinal products,
   wherein said medicinal product is formulated for oral, nasal, vaginal, ocular, subcutaneous, intravenous, intramuscular, intradermal, intraperitoneal or intracerebral administration,
   wherein said active principle is selected from the group consisting of proteins, glycoproteins, proteins linked to one or more polyalkylene glycol chains, peptides, polysaccharides, liposaccharides, oligonucleotides, small organic molecules that are hydrophobic, small organic molecules that are hydrophilic and small organic molecules that are amphiphilic.

24. The polyamino acid of claim 2, wherein the sum of n+m ranges from 30 to 300.

* * * * *